United States Patent [19]
Van der Ende

[11] Patent Number: 5,822,814
[45] Date of Patent: Oct. 20, 1998

[54] MEDICAL DIAGNOSTIC AND/OR THERAPY APPARATUS WITH A SWINGABLE PATIENT TABLE TOP

[75] Inventor: Adrianus Van der Ende, Eindhoven, Netherlands

[73] Assignee: U.S. Philips Corporation, New York, N.Y.

[21] Appl. No.: 870,220

[22] Filed: Jun. 6, 1997

[30] Foreign Application Priority Data

Jun. 14, 1996 [BE] Belgium .............................. 09600550

[51] Int. Cl.$^6$ ...................................................... H05G 1/02
[52] U.S. Cl. .................................. 5/601; 5/611; 378/179; 378/209
[58] Field of Search .................................. 5/601, 611, 11, 5/600; 378/179, 209

[56] References Cited

U.S. PATENT DOCUMENTS

| | | | |
|---|---|---|---|
| 4,360,936 | 11/1982 | Keller | 5/11 |
| 4,885,998 | 12/1989 | Span et al. | 5/611 X |
| 5,013,018 | 5/1991 | Sicele et al. | 5/601 |
| 5,014,292 | 5/1991 | Siczek et al. | 378/196 |
| 5,029,826 | 7/1991 | Schaefer | 5/600 |
| 5,410,767 | 5/1995 | Barud | 5/601 |

*Primary Examiner*—Michael F. Trettel
*Attorney, Agent, or Firm*—Dwight H. Renfrew, Jr.

[57] ABSTRACT

A medical diagnostic and/or therapy apparatus in the form of an X-ray apparatus, including a stand (2), a C-arm (4) and a patient table top (8) which is attached to the stand by way of a supporting arm (6). In order to enable the patient table top to be cleared very quickly from the C-arm (i.e. make it accessible from all sides), notably in trauma situations, the supporting arm of the patient table is rotatable about a vertical axis (22) with respect to the stand. The pivot (25) of the supporting arm is situated at the location of attachment of the supporting arm to the stand, so that when it is swung away, the table requires substantially less space in its longitudinal direction than in the prior art. Moreover, room then remains for an additional treatment apparatus in the treatment space, for example for a tomography arc (26) which can then be positioned around the swung away table top within a few seconds in the case of emergency.

20 Claims, 2 Drawing Sheets

MEDICAL DIAGNOSTIC AND/OR THERAPY APPARATUS WITH A SWINGABLE PATIENT TABLE TOP

BACKGROUND OF THE INVENTION

1. Field of the Invention

The invention relates to a medical diagnostic and/or therapy apparatus, including

- a component support for diagnostic and/or therapy components,
- a patient table top, and
- a stand for supporting the patient table top and the component support,
  - the patient table top being attached to the stand by way of a supporting arm which is provided with a pivot for pivoting about a substantially vertical axis.

2. Description of Related Art

An apparatus of this kind is known from U.S. Pat. No. 5,014,292. The apparatus described therein is an X-ray examination apparatus which includes a stand with an arc-shaped component support for an X-ray tube and an X-ray image intensifier which in this case constitute the diagnostic and/or therapy components. In order to form an X-ray image of the patient to be examined, the patient can be arranged between the X-ray tube and the X-ray image intensifier by way of a patient table top which is displaceable in a variety of directions in order to obtain the appropriate orientation and position of the patient relative to the X-ray tube and the X-ray image intensifier. The patient table top is also attached to the stand, that is to say by way of a supporting arm which is connected to the table top via a hinge having a substantially vertical axis. The pivot of the hinge is situated at the end of the supporting arm, i.e. at the location where the supporting arm is attached to the table top.

The patient table top can be swung away in a substantially horizontal plane by rotating the table top about said vertical axis, so that it is no longer situated between the X-ray tube and the X-ray image intensifier and hence clears the arc-shaped component support. In this situation the component support can be rotated, so that the X-ray tube and the X-ray image intensifier can change places. Moreover, the attending staff is thus offered more standing room around the table top. The latter is important notably in the case of trauma situations, because in such situations the patient must be very quickly accessible from all sides.

Swinging away the table top attached to the stand also makes it possible to position regions of the patient between the X-ray tube and the X-ray image intensifier tube for which the patient would have to be displaced, for example the arm or the side of the torso. This is undesirable particularly in the case of trauma patients.

Trauma patients entering the operating room on a mobile stretcher from an ambulance can now be arranged directly between the X-ray tube and the X-ray image intensifier. The transfer from the stretcher to the table top, particularly undesirable in the case of trauma patients, is then no longer necessary because the table top is swung away so that the stretcher can take its place.

Finally, swinging away the patient table enables other diagnostic and/or therapy components, for example a circular arm for computer tomography, to be arranged around the patient. Such an arm may be a mobile type which can be arranged near a wall of the operating room. If this component has to be used during treatment of a patient, the patient table is swung one quarter of a turn in the direction of the tomography arm which can then be arranged around the patient from one end of the table top by displacement in one direction. In trauma situations, therefore, changing-over from X-ray fluoroscopy to tomography can take place within a few seconds, without it being necessary to displace the patient on the table top.

In the known diagnostic and/or therapy apparatus the pivot of the hinge is situated at a short side of the table top, i.e. at an end there of, at some distance from a corner point of the table top at the side of the stand, whereas the supporting arm is non-rotatably attached to the stand. Because of the attachment of the table top to the supporting arm and of the supporting arm to the stand, a problem of space may occur in the treatment room. In the swung away position the longitudinal direction of the table top extends in the prolongation of the supporting arm, so that in this direction the apparatus occupies a space amounting to the sum of the width of the stand, the length of the supporting arm and the length of the patient table. Furthermore, in this direction in the treatment room space must be reserved for the (mobile) tomography arc. Because the latter apparatus has to be put into use so quickly, it must be stationed at the end of the swung away patient table, so that it can be positioned around the patient in one motion. If this apparatus were stationed elsewhere in the treatment room, it would be necessary to manoeuvre it between the attending staff in frantic situations in the treatment room with a floor often cluttered with cables for the equipment. Because the treatment rooms have standard dimensions in practically all hospitals, changing the dimensions of such treatment rooms is not possible or at least very expensive.

SUMMARY OF THE INVENTION

It is an object of the invention to provide a solution to the described problem of space; to this end, the medical diagnostic and/or therapy apparatus according to the invention is characterized in that the pivot is provided in the supporting arm at a distance from the stand which amounts to less than half the length of the supporting arm.

As a result of this step, when the patient table is swung away from between the X-ray tube and the X-ray image intensifier of the apparatus, it will occupy a space in the longitudinal direction which only amounts to the sum of the width of the stand, at the most half the length of the supporting arm, and the length of the patient table. The space required is thus substantially reduced.

The space required can be further reduced in a preferred embodiment of the invention. In this embodiment the pivot is situated at the location of attachment of the supporting arm to the stand. As a result of this step, a saving of space amounting to the length of the supporting arm is achieved in comparison with the state of the art.

BRIEF DESCRIPTION OF THE DRAWINGS

The invention, including further attractive embodiments, will be described in detail hereinafter with reference to the drawing, in which corresponding reference numerals denote corresponding elements. Therein.

DETAILED DESCRIPTION OF THE PREFERRED EMBODIMENTS

Figure 1:
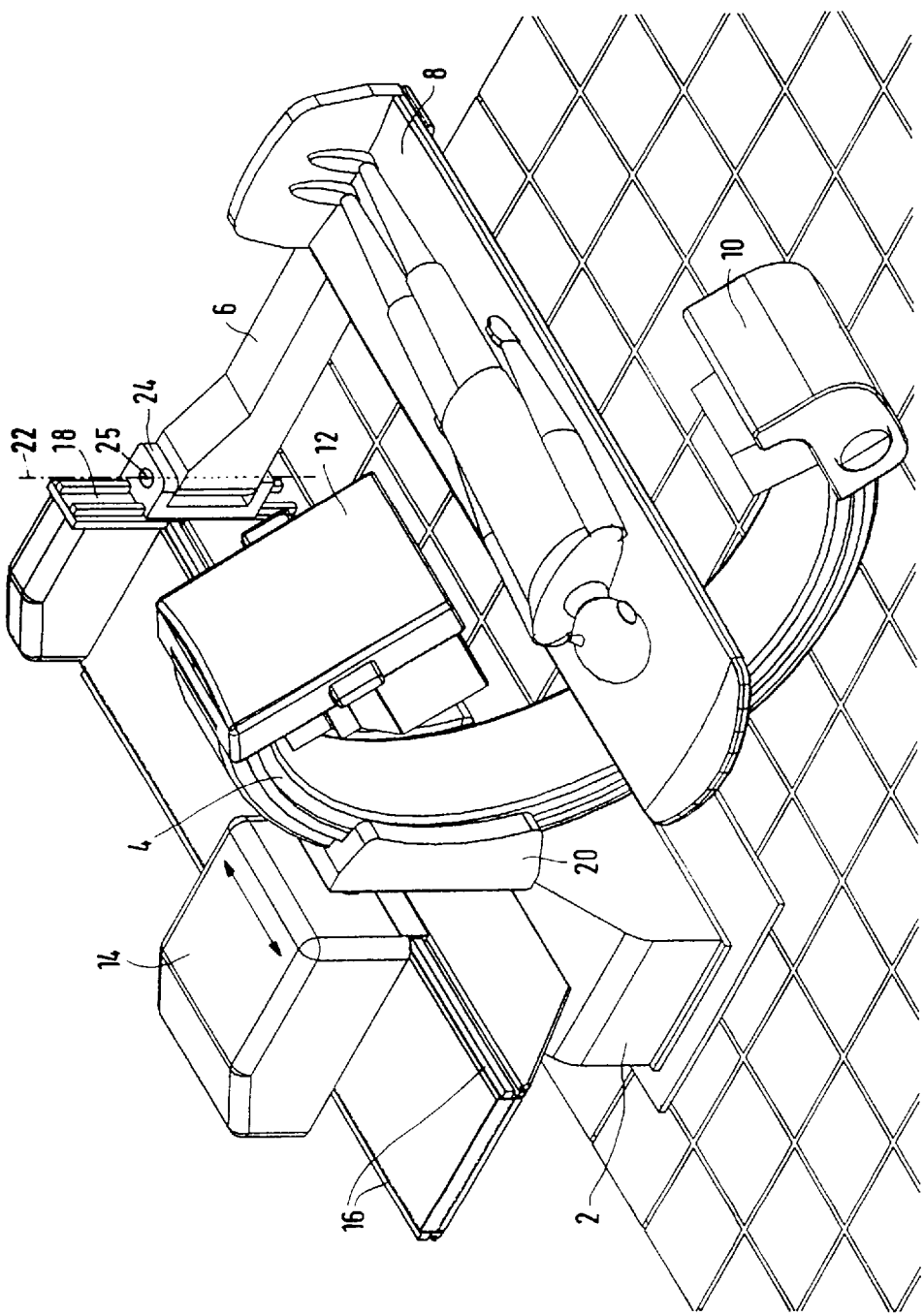
FIG. 1 is a perspective view of a medical diagnostic and/or therapy apparatus according to the invention.

FIG. 1 is a perspective view of a medical diagnostic and/or therapy apparatus according to the invention installed in a medical treatment room. The apparatus consists of a stand 2, a component support 4 for diagnostic and/or therapy components, and a patient table top 8 which is connected to the stand, via a supporting arm 6, and serves to carry the patient to be treated. The component support 4 is in this case formed by a C-arm and the diagnostic and/or therapy components are formed by an X-ray source 10 and an X-ray detector 12 which are mounted on the C-arm. The C-arm 4 is attached to a carriage 14 which is displaceable in the longitudinal direction (as denoted by the arrow on the carriage). The C-arm can thus be displaced on the stand 2 via a guide 16. The C-arm is also rotatable in its own plane by way of a trackway 20 and the trackway 20 itself is also rotatable about an axis extending according to a center line of the C-arm. The X-ray tube and the X-ray image intensifier can thus be adjusted in such a manner that the patient to be treated can be irradiated in all desired directions and from all desired positions.

The height of the patient table 8 can be adjusted by means of a vertical guide 18 along which the supporting arm 6 can move up and down. The supporting arm is also rotatable about a vertical axis 22. This axis constitutes the pivot 25 of a hinge 24 whose stationary part is connected to the stand 2 and whose movable part is formed by the end of the supporting arm 6.

Figure 2:
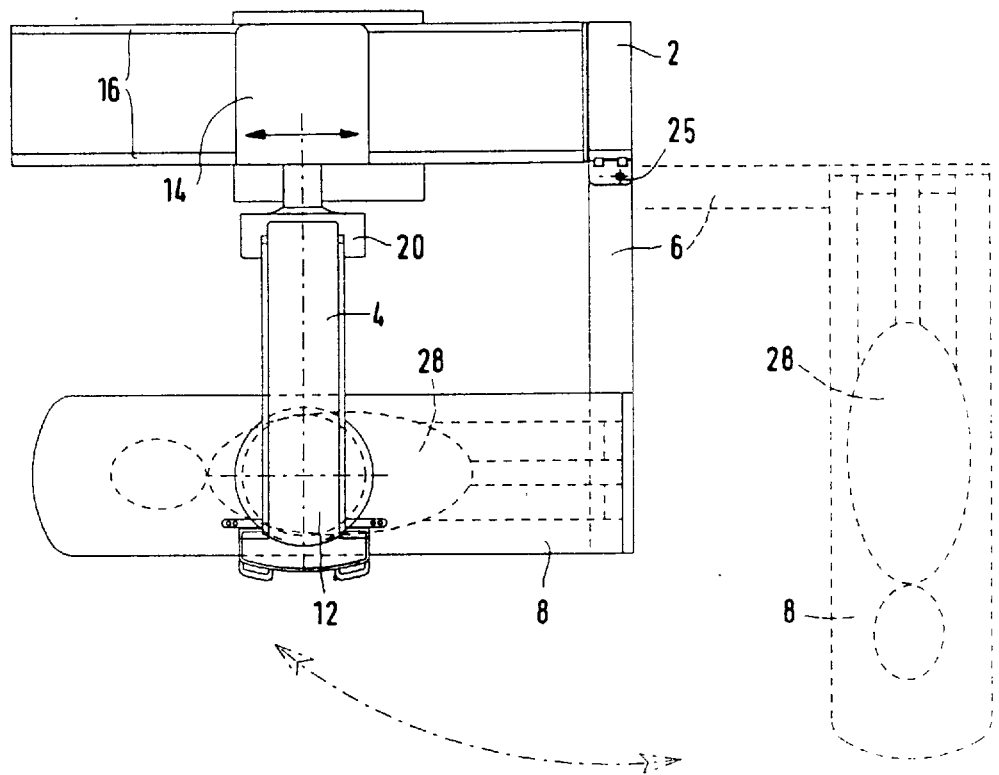
FIG. 2 is a plan view of the medical diagnostic and/or therapy apparatus according to the invention, the patient table top also being shown in the swung away position.
Figure 2:
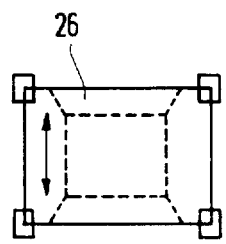

FIG. 2 is an elementary plan view of the medical diagnostic and/or therapy apparatus according to the invention, the patient table top 8 also being shown in the swung away position. In this Figure the swung away position of the patient table top 8 and of the supporting arm 6 are shown in dashed lines.

Locking means (not shown in the Figure) may be provided for locking the position of the patient table top 8 swung away around the pivot 25, so that the table remains locked in the swung away position during treatment of the patient. Moreover, electric switching means (not shown in the Figure) may be provided to prevent the component support 4 from being driven in the swung away position of the patient table top 8. These switching means are activated by movement of the patient table top 8 relative to the supporting arm 6. This prevents accidental movement of the component support while the attending staff is gathered around the swung away table top.

This Figure also shows the parking position of a mobile tomography arm 26. If the patient 28 must be very quickly accessible from all sides (notably in trauma situations), the attending staff can gather around the table top when the patient table top 8 is swung away to the position shown in dashed lines. Moreover, because the patient table 8 is swung out, a circular arm 26 for computer tomography can then be arranged around the patient. This arm is constructed so as to be mobile and is normally placed against a wall of the treatment room. If it appears necessary to use this component during treatment of a patient, the patient table is swung one quarter of a turn in the direction of the tomography arm 26; the arm can then be arranged around the table top with the patient by displacing it in one direction. Thus, changing over from fluoroscopy to tomography can take place within a few seconds, without it being necessary to displace the patient on the table top. Because the pivot 25 is situated at the location of attachment of the supporting arm 6 to the stand 2 (and not at the location of attachment of the supporting arm to the patient table top as in the prior art), the space required for the entire apparatus according to the invention in the longitudinal direction of the swung away table is substantially smaller than in the known situation; in the swung away situation nevertheless sufficient space remains for the attending staff to stand around the table and to position an additional treatment apparatus such as a tomography arm 26.

It is claimed:

1. A medical diagnostic and/or therapy apparatus, comprising a component support for diagnostic and/or therapy components, a patient table top, and a stand for supporting the patient table top and the component support, the patient table top being attached to the stand by way of a supporting arm which is provided with a pivot for pivoting about a substantially vertical axis, which pivot is provided in the supporting arm at a distance from the stand which amounts to less than half the length of the supporting arm, and wherein the component support is displaceably mounted on the stand for longitudinal motion along the length of and parallel to the patient table top when the patient table top has been swung around the pivot toward the stand.

2. An apparatus as claimed in claim 1, wherein the pivot is situated at the location of attachment of the supporting arm to the stand.

3. An apparatus as claimed in claim 2, in which the pivot is formed by a hinge.

4. An apparatus as claimed in claim 3, in which locking means are provided for locking the position of the patient table top after swinging out around the pivot.

5. An apparatus as claimed in claim 4, further comprising switching means which can be activated by motion of the patient table in order to prevent driving of the component support when the patient table top has been swung out around the pivot.

6. An apparatus as claimed in claim 3, further comprising switching means which can be activated by motion of the patient table in order to prevent driving of the component support when the patient table top has been swung out around the pivot.

7. An apparatus as claimed in claim 2, in which locking means are provided for locking the position of the patient table top after swinging out around the pivot.

8. An apparatus as claimed in claim 7, further comprising switching means which can be activated by motion of the patient table in order to prevent driving of the component support when the patient table top has been swung out around the pivot.

9. An apparatus as claimed in claim 2, further comprising switching means which can be activated by motion of the patient table in order to prevent driving of the component support when the patient table top has been swung out around the pivot.

10. An apparatus as claimed in claim 1, wherein the pivot is formed by a hinge.

11. An apparatus as claimed in claim 3, in which locking means are provided for locking the position of the patient table top after swinging out around the pivot.

12. An apparatus as claimed in claim 11, further comprising switching means which can be activated by motion of the patient table in order to prevent driving of the component support when the patient table top has been swung out around the pivot.

13. An apparatus as claimed in claim 10, further comprising switching means which can be activated by motion of the patient table in order to prevent driving of the component support when the patient table top has been swung out around the pivot.

14. An apparatus as claimed in claim 1, further comprising locking means for locking the position of the patient table top after swinging out around the pivot.

15. An apparatus as claimed in claim 14, further comprising switching means which can be activated by motion of the patient table in order to prevent driving of the component support when the patient table top has been swung out around the pivot.

16. An apparatus as claimed in claim 1, further comprising switching means which can be activated by motion of the patient table in order to prevent driving of the component support when the patient table top has been swung out around the pivot.

17. A medical diagnostic and/or therapy apparatus, comprising a component support for diagnostic and/or therapy components, a patient table top, a stand for supporting the patient table top and the component support, the patient table top being attached to the stand by way of a supporting arm which is provided with a pivot for pivoting about a substantially vertical axis, which pivot is provided in the supporting arm at a distance from the stand which amounts to less than half the length of the supporting arm, and locking means for locking the position of the patient table top after swinging out around the pivot.

18. An apparatus as claimed in claim 17 further comprising switching means which can be activated by motion of the patient table top in order to prevent driving of the component support when the patient table top has been swung out.

19. A medical diagnostic and/or therapy apparatus, comprising a component support for diagnostic and/or therapy components, a patient table top, a stand for supporting the patient table top and the component support, the patient table top being attached to the stand by way of a supporting arm which is provided with a pivot for pivoting about a substantially vertical axis, which pivot is provided in the supporting arm at a distance from the stand which amounts to less than half the length of the supporting arm, and switching means which can be activated by motion of the patient table top in order to prevent driving of the component support when the patient table top has been swung out.

20. An apparatus as claimed in claim 19 further comprising locking means for locking the position of the patient table top after swinging out around the pivot.

* * * * *